(12) United States Patent
Field

(10) Patent No.: US 8,568,775 B2
(45) Date of Patent: Oct. 29, 2013

(54) TABLET OF PARACETAMOL CONTAINING AN ENCAPSULATED FLAVORANT

(75) Inventor: Paul Frederick Field, Hull (GB)

(73) Assignee: Reckitt Benckiser Healthcare (UK) Limited, Slough, Berkshire (GB)

( * ) Notice: Subject to any disclaimer, the term of this patent is extended or adjusted under 35 U.S.C. 154(b) by 602 days.

(21) Appl. No.: 12/295,771

(22) PCT Filed: Apr. 2, 2007

(86) PCT No.: PCT/GB2007/001202
§ 371 (c)(1),
(2), (4) Date: Apr. 27, 2009

(87) PCT Pub. No.: WO2007/113536
PCT Pub. Date: Oct. 11, 2007

(65) Prior Publication Data
US 2009/0220594 A1    Sep. 3, 2009

(30) Foreign Application Priority Data
Apr. 5, 2006  (GB) .................................. 0606848.0

(51) Int. Cl.
*A61K 9/20* (2006.01)
*A61K 9/46* (2006.01)
*A61K 31/167* (2006.01)

(52) U.S. Cl.
USPC ............................ 424/465; 424/466; 514/630

(58) Field of Classification Search
None
See application file for complete search history.

(56) References Cited

U.S. PATENT DOCUMENTS

| 4,562,024 | A | | 12/1985 | Rogerson | |
|---|---|---|---|---|---|
| 4,597,959 | A | | 7/1986 | Barr | |
| 4,968,509 | A | * | 11/1990 | Radebaugh et al. | 424/470 |
| 5,348,745 | A | * | 9/1994 | Daher | 424/466 |
| 5,348,747 | A | * | 9/1994 | Bianco | 424/490 |
| 5,370,878 | A | * | 12/1994 | Shah | 424/469 |
| 5,424,075 | A | * | 6/1995 | Daher et al. | 424/465 |
| 5,656,293 | A | * | 8/1997 | Daher et al. | 424/465 |
| 5,773,031 | A | * | 6/1998 | Shah et al. | 424/497 |
| 5,814,339 | A | * | 9/1998 | Prudhoe | 424/480 |
| 5,976,577 | A | | 11/1999 | Green et al. | |
| 6,426,090 | B1 | | 7/2002 | Ream et al. | |
| 6,482,433 | B1 | | 11/2002 | DeRoos et al. | |
| 6,485,747 | B1 | * | 11/2002 | Flanagan et al. | 424/479 |
| 6,607,750 | B2 | * | 8/2003 | Upadhyay et al. | 424/464 |
| 6,669,957 | B1 | | 12/2003 | Laruelle et al. | |
| 7,101,572 | B2 | * | 9/2006 | Santos et al. | 424/486 |
| 2001/0008635 | A1 | | 7/2001 | Quellet et al. | |
| 2005/0276847 | A1 | * | 12/2005 | Roberts et al. | 424/464 |
| 2007/0141144 | A1 | * | 6/2007 | Roberts et al. | 424/464 |
| 2007/0154549 | A1 | * | 7/2007 | Morton et al. | 424/470 |
| 2008/0102116 | A1 | * | 5/2008 | Perry et al. | 424/465 |

FOREIGN PATENT DOCUMENTS

| CN | 1176784 A | 3/1998 |
|---|---|---|
| DE | 19502789 A1 | 1/1996 |
| EP | 0695546 A1 | 2/1996 |
| EP | 0922449 A2 | 6/1999 |
| EP | 1064856 A2 | 1/2001 |
| WO | WO 2005/063203 | 7/2005 |

OTHER PUBLICATIONS

Buhler, V. Polyvinylpyrrolidone excipients for pharmaceuticals. Springer-Verlag (2005) ch. 3, pp. 136-172.*
AbuBaker et al. "Copovidone" in Handbook of Pharmaceutical Excipients. Pharmaceutical Press (Fifth Edition) 2006; 201-203.*
UK Search & Examination Report dated Jul. 28, 2006.
UK Examination Report dated Nov. 5, 2008.
UK Examination Report dated Jul. 21, 2009.
Dr. F. Heinze, "New Opportunities—Speciality Pregelatinised Starch Excipients" Samedan Ltd Pharmaceutical Publishers, 2002.
S. Qi, "An Investigation into the Recrystallization Behaviour of Amorphous Paracetamol", JPP 2005, 57 (Supplement), Abstract 212, pp. 92-94.
International Search Report, Application No. PCT/GB2007/001202, by Examiner Raquel Paul Soto, dated Jun. 20, 2007.

* cited by examiner

*Primary Examiner* — Daniel Sullivan
*Assistant Examiner* — Peter Anthopolos
(74) *Attorney, Agent, or Firm* — Troutman Sanders LLP; Ryan A. Schneider

(57) ABSTRACT

A medicament tablet containing paracetamol (acetaminophen) as the (or an) active ingredient, and an encapsulated flavorant. The tablet may be swallowed in tablet form or may be dissolved or dispersed in water to form a palatable drink.

8 Claims, No Drawings

US 8,568,775 B2

TABLET OF PARACETAMOL CONTAINING AN ENCAPSULATED FLAVORANT

CROSS REFERENCE TO RELATED APPLICATIONS

This application is the National Stage of International Application No. PCT/GB2007/001202 filed on 2 Apr. 2007, which claims priority to British Patent Application No. 0606848.0 filed on 5 Apr. 2006. The contents of both applications are hereby incorporated by reference in their entireties.

FIELD OF THE INVENTION

This invention relates to a medicament product, and in particular to a compressed medicament tablet. The invention further relates to a method of manufacturing a compressed medicament tablet.

BACKGROUND

A number of commercially available analgesic products are flavoured. Among such products commercially available in the UK are BOOTS Cold Relief Hot Blackcurrant/Lemon and the LEMSIP range from Reckitt Benckiser (registered trade marks). Analgesic products flavoured with fruit flavorants, especially those reproducing sharp flavours such as blackcurrant and lemon, have excellent consumer acceptance.

However the incorporation of flavorants is not absolutely straightforward. Most flavorants are oil-based and are moderately volatile. Many tablets are made by a process which includes wet granulation, involving a drying step. If an oil-based flavorant is present during the drying step it may be lost, completely or in part. Furthermore, when analgesic tablets contain paracetamol as the (or an) active ingredient the process is inherently difficult; paracetamol is, simply, a difficult material to tablet. When an oil-based flavorant is added to paracetamol, it tends to increase the difficulties in tabletting; the oleophilic qualities of the flavorant act to increase the difficulty in getting particles to adhere together.

Thus, in an internet article called "New Opportunities—Speciality Pregelatinised Starch Excipients" by Dr F Heinze, at: www.samedanltd.com/members/archives/PMPS/Autumn2002/FredHeinze.htm Dr Heinze states "Wet granulation is the chosen method for poorly compressible drugs such as Acetaminophen (paracetamol)".

Additionally, U.S. Pat. No. 4,562,024 concerns an improved wet granulation process for preparing compressed tablets, particularly those containing a "poorly compressible medicament e.g. paracetamol".

In the British Pharmaceutical Society (BPS) 2005 Science Abstracts, Abstract 212 which is available online at www.rps-gb.org.uk/pdfs/bpc05sciabs204-212.pdf; called "An Investigation into the Recrystallization Behaviour of Amorphous Paracetamol", the authors S. Qi and D. Q. M. Craig, of the School of Chemical Sciences and Pharmacy, University of East Anglia, UK, state that paracetamol is known to exist in three polymorphic forms, including the stable monoclinic form I which has "poor tabletting properties".

Thus, starting points for the present invention are that paracetamol is difficult to tablet, and that paracetamol tablets are conventionally made by a wet granulation process; consequently flavorants are difficult to incorporate. Adding them too early in the manufacturing process causes loss of flavorant.

SUMMARY OF THE INVENTION

In accordance with a first aspect of the present invention there is provided a medicament tablet containing paracetamol as the (or an) active ingredient, and an encapsulated flavorant.

Encapsulated flavorants are commercially available. It is known that they may assist in giving a product a longer shelf-life. We have realised, and shown, that when an encapsulated flavorant is used there is much greater flexibility in terms of the manufacturing process for a paracetamol medicament.

For example, when an encapsulated flavorant is used it may be added at any stage, even when wet granulation is carried out. That is, it can withstand the drying step which is needed, without loss or damage.

However, by use of a suitable encapsulated flavour and other ingredients, direct tabletting may be employed (and is preferred), without granulation taking place at all. That is to say, as-supplied ingredients (which may generally be in the form of powders but with the flavorant being in its encapsulated particulate form) may be mixed, then pressed. We have found that tablets of good mechanical properties can be obtained in this way.

In accordance with a second aspect of the present invention there is provided a method of making a tablet containing a paracetamol medicament, the method comprising the compression of powder or granular materials including paracetamol and an encapsulated flavorant.

Preferably the method comprises the direct compression of the ingredients.

Preferably the method does not include a heating or warming step.

Preferably the method does not include wet granulation.

Preferably a pressing aid is present. Especially preferred is a fatty acid or fatty acid ester, for example a stearate salt, preferably magnesium stearate.

Preferably the method includes the addition of an encapsulated flavorant substantially at the stage when paracetamol is mixed with the other ingredients.

In accordance with a third aspect of the present invention there is provided the use of an encapsulated flavorant in the manufacture of a paracetamol medicament.

DETAILED DISCLOSURE

The following statements and definitions apply to any or all of the first, second, third or fourth aspects of the present invention, as the context permits.

The encapsulated flavorant can with advantage be added with the other ingredients at the start of the mixing process (a substantial manufacturing advantage). The flavour sensation to the eventual customer may be good whether administered in drink form or in tablet form.

The tablets may contain a second analgesic medicament, of which favoured examples are ibuprofen; flurbiprofen; buprenorphine; aspirin; codeine; celecoxib; diclofenac; ketoprofen; meloxicam; naproxen; and rofecoxib. Such compounds may be in the form stated or in the form of an optical isomer, salt or ester. For example ibuprofen may be in the form of ibuprofen acid, or in the form of an ibuprofen salt such as sodium ibuprofen, or lysine ibuprofen.

The paracetamol which is used may be coated with pre-gelatinised starch.

The tablet may contain a URT (upper respiratory tract) aid. A URT aid may be an active agent which assists in combating a cold, sore throat, cough or influenza. A URT aid include a decongestant, a cough suppressant (or antitussive), and an expectorant (or mucolytic agent). Suitable URT aids fulfilling one or more of the above-mentioned functions include: oxymetazoline, phenylephrine, pseudoephedrine, and diphenhydramine (examples of decongestants); dextromethorphan, noscapine, ethyl morphine, theobromine, pholcodine, and codeine (examples of cough suppressants); and guaifenesin and ambroxol (examples of expectorants). Such compounds may be in the form stated or in the form of an optical isomer, salt or ester. For example several of the compounds are commonly supplied in the form of their hydrochloride salt.

A preferred tablet of the present invention is one which is suitable to be swallowed in the tablet form but which also dissolves quickly in water to produce a palatable drink. Preferably the tablet can be swallowed in the tablet form without substantial or discomforting dissolution or disintegration in the mouth. Yet, preferably such a tablet dropped into a glass of water dissolves or disperses, with gentle stirring of the water, within 2 minutes, preferably within 1 minute, and most preferably within 30 seconds. Preferably this is the case when the water is at 60° C. (a reasonable reference test in relation to use to produce a hot drink). Preferably it also applies, alternatively or additionally, to water at 25° C. or 37° C., which some tests use as a reference temperature. Most preferably it dissolves or disperses within the stated time periods in water both at 25° C. or 37° C. or 60° C.

Preferably such a tablet contains a disintegration aid. The disintegration aid could be a material or materials that produce effervescence when the tablet is placed in water. Thus, the tablet could contain an effervescent couple, typically an ingestible acid and an ingestible base, which react together in water to liberate carbon dioxide. The liberated carbon dioxide assists in the break-up of the tablet. This type of disintegration aid is, of course, well known but is not the most preferred approach for the present invention, because it could produce undesirable effervescence in the saliva in the mouth, if a patient is slow to swallow the tablet.

Therefore, a more preferred disintegration type for use in this aspect of the invention is a non-effervescent disintegration aid; preferably a water-swellable material. Most preferred is a water-swellable polymer. A number of such materials are known, and are generally based on cross-linked polymers of N-vinyl-2-pyrrolidone compounds or on cellulosic compounds which have been chemically modified to enhance their water uptake capacity. Especially preferred are croscarmellose sodium or carboxymethylcellulose (SCMC), low-substituted hydroxypropyl cellulose (L-HPC) and, especially, crospovidone.

Preferably the tablet contains a binder, for example a starch or cellulose derivative or a sugar alcohol. Many binders are known to the person skilled in the art but especially preferred for use in the tablets of the present invention is microcrystalline cellulose.

In addition to the encapsulated flavourant the tablet preferably contains a further flavouring agent, preferably an organic acid flavourant or salt thereof, non-encapsulated, for example citric acid, tartaric acid, malic acid, maleic acid, fumaric acid or ascorbic acid; or a salt of any of the foregoing (preferably an alkali metal salt). A polycarboxylic acid, preferably containing 2-4 carboxylic groups per molecule, is preferred; in particular citric acid.

In addition to the encapsulated flavourant and optionally a non-encapsulated organic acid flavourant or salt thereof the tablet preferably contains a further flavouring agent, in the form of a sweetening agent. A preferred sweetening agent is an intense synthetic or semi-synthetic sweetener, for example acesulfame potassium, sucralose, saccharin, neotame or, preferably, aspartame.

We have found, to our surprise, that when an encapsulated flavorant is employed it can be flavoured in a way which is good when the tablet is to be swallowed as such, and which is also good when the tablet is dissolved in water to form a drink (for example a drink of volume 50-150 ml). We expected that the flavour would be too intense when the tablet was to be swallowed as such, and too weak in the drink form. Or, if one mode was formulated to be optimal, the other mode would be quite unsuitable. We were surprised to determine that the flavour sensation both in the tablet form and in the drink form was good; sufficiently good that the resulting tablet was one with a potential to be offered for sale, with a recommendation for both types of administration.

Preferably a tablet of the invention has a friability of up to 2%, preferably up to 1%, and most preferably up to 0.5%, as determined by Ph Eur monograph method 2.9.7.

Preferably a tablet of the invention has a hardness of at least 8 kp, preferably at least 10 kp, and most preferably at least 14 kp, as determined by Ph Eur monograph method 2.9.8.

Preferably a tablet of the invention has a hardness of up to 26 kp, preferably up to 22 kp, and most preferably up to 18 kp, as determined by Ph Eur monograph method 2.9.8.

Preferably a tablet of the invention is at least 700 mg in weight, preferably at least 780 mg, most preferably at least 860 mg.

Preferably a tablet of the invention is up to 1400 mg in weight, preferably up to 1200 mg, most preferably up to 1100 mg.

Preferably a tablet of the invention comprises at least 200 mg paracetamol, more preferably at least 300 mg, and most preferably at least 400 mg.

Preferably a tablet of the invention comprises up to 800 mg paracetamol, more preferably up to 700 mg, and most preferably up to 600 mg.

Most preferably the tablet contains 500-550 mg paracetamol.

Preferably a tablet of the invention comprises at least 40 mg of encapsulated flavorant, preferably at least 80 mg, preferably at least 100 mg.

Preferably a tablet of the invention comprises up to 240 mg of encapsulated flavorant, preferably up to 200 mg, preferably up to 150 mg.

When a URT aid is present it is preferably present in an amount of at least 2 mg, preferably at least 4 mg, most preferably at least 5 mg.

When a URT aid is present it is preferably present in an amount of up to 200 mg, preferably up to 100 mg, most preferably up to 50 mg, especially up to 30 mg.

When a disintegration aid is present it is preferably present in an amount of at least 20 mg, preferably at least 40 mg, most preferably at least 60 mg.

When a disintegration aid is present it is preferably present in an amount of up to 200 mg, preferably up to 140 mg, most preferably up to 100 mg.

When a binder is present it is preferably present in an amount of at least 20 mg, preferably at least 40 mg, most preferably at least 60 mg.

When a binder is present it is preferably present in an amount of up to 200 mg, preferably up to 140 mg, most preferably up to 100 mg.

When a pressing aid is present it is preferably present in an amount of at least 2 mg, preferably at least 4 mg, most preferably at least 5 mg.

When a pressing aid is present it is preferably present in an amount of up to 50 mg, preferably up to 20 mg, most preferably up to 10 mg.

When an organic acid or salt thereof is present as a further flavourant it is preferably in an amount of at least 10 mg, preferably at least 25 mg, most preferably at least 40 mg.

When an organic acid or salt thereof is present it is preferably present in an amount of up to 100 mg, preferably up to 80 mg, most preferably up to 60 mg.

When a sweetening agent is present it is preferably present in an amount of at least 10 mg, preferably at least 20 mg, most preferably at least 30 mg.

When a sweetening agent is present it is preferably present in an amount of up to 80 mg, preferably up to 65 mg, most preferably up to 50 mg.

In accordance with a fourth aspect of the present invention there is provided a medicament tablet comprising (and in a preferred embodiment consisting essentially of) the following components in the amounts stated:
paracetamol, 200-800 mg;
encapsulated flavourant, 40-240 mg;
disintegration aid, 20-200 mg;
binder, 20-200 mg;
pressing aid, 2-50 mg;
organic acid/salt flavourant, 10-100 mg; and
sweetening agent, 10-80 mg;
but in such amounts that the tablet weight is within the defined weight range;
wherein the tablet has the following characteristics:
its weight is in the range 700-1400 mg;
its friability does not exceed 2% as determined by Ph Eur monograph method 2.9.7;
its hardness is in the range 8-26 kp as determined by Ph Eur monograph method 2.9.8;
it is palatable when taken as a tablet; and
it dissolves quickly in water to produce a palatable drink.

The tablet of the fourth aspect may additionally contain 2-200 mg of a URT aid.

There may be more than one component of a designated type; for example more than one URT aid, or more than one sweetening agent. In all such cases the amounts stated in the definitions and claims herein (for example binder, 20-200 mg; sweetening agent, 10-80 mg) represent the summation of such components.

The invention will now be further described, by way of example only.

In relation to the encapsulated flavourant we do not believe that the nature of the encapsulation is critical. Rather, we believe that the most important thing is simply the fact that the flavourant is encapsulated; and so is segregated from the paracetamol, and preferably from the other components of the tablet mentioned herein.

Thus we do not believe the chemical nature of the encapsulant to be critical to this invention. We believe that there are many disclosures of encapsulated flavourants which would be suitable, and of methods of making them. The nature of the encapsulated flavorant is not of the essence of this invention. Reference may be made to published patent specifications if further information is desired. Broadly, all encase the flavour source in a shell or compound it in a matrix, which is then comminuted to form particulate material.

The flavour ingredient encapsulated is preferably a hydrophobic flavour ingredient or composition of current use.

The term flavour ingredient as used herein is deemed to define a variety of flavour materials of both natural and synthetic origin. They include single compounds and mixtures. The system of the invention may encapsulate volatile or labile components which may be in liquid or solid form, preferably hydrophobic. Specific examples of such components may be found in the current literature, e.g. in Perfume and Flavour Chemicals by S. Arctander, 1969, Montclair N.J. (USA); Fenaroli's Handbook of Flavour Ingredients, 1975, CRC Press or Synthetic Food Adjuncts, 1947, by M. B. Jacobs, van Nostrand Co., Inc.

Suitable natural extracts which can be encapsulated for use in the present invention include citrus extracts such as lemon, orange, lime, grapefruit or mandarin oils; berry and currant extracts such as blackcurrant, raspberry and strawberry; cocoa, mint and vanilla essences; and essential oils of herbs or spices.

The proportion of flavour ingredient in the encapsulating matrix is preferably comprised between 0.1 and 25% by weight relative to encapsulated flavourant, and preferably between 5 and 16%. An emulsifier agent may suitably be present, in proportions varying typically from 0.1 to 10%, and preferably from 0.4 to 2%, relative to the solid product. Typical examples include soya lecithin and citric acid esters of fatty acids, but other suitable emulsifiers are cited in reference texts such as Food Emulsifiers and Their Applications, 1997, edited by G. L. Hasenhuettl and R. W. Hartel, USA.

One encapsulation technology employs small amounts of agar agar, e.g. 1-7%, in combination with a carbohydrate material, in the composition of the matrix of an extruded system. The carbohydrate material used in combination with agar agar can be any sugar or sugar derivative which can be readily processed through extrusion techniques to form a dry extruded solid. Particular examples of suitable materials include those selected from the group consisting of sucrose, glucose, lactose, levulose, fructose, maltose, ribose, dextrose, isomalt, sorbitol, mannitol, xylitol, lactitol, maltitol, pentatol, arabinose, pentose, xylose, galactose, hydrogenated starch hydrolysate or succinylated, chemically modified starch, corn syrup, maltodextrin, polydextrose and derivatives and mixtures thereof. In one particular embodiment of the invention the carbohydrate material is selected from the group consisting of maltodextrin or a corn syrup, a chemically modified starch, a hydrogenated starch hydrolysate or a succinylated or hydrolyzed starch. Preferably, the maltodextrin used has a dextrose equivalent (DE) of at least 18. In specific embodiments, there will be used polymeric carriers which include maltodextrin. The latter can be the main carbohydrate material of the matrix, or yet, be used in admixture with any one of the sugars mentioned above, preferably sucrose.

In another approach a colloid gel may first be formed by dissolving gelatin in water at an appropriate temperature. This temperature is usually determined by the gelling temperature of the selected gelatin or other polymers. The mixture is mixed with a high sheer mixer such as Breddo Likwifier (American Ingredients Co., 550 South 18th St., Kansas City, Kans. 66105-1104) to dissolve the gelatin completely. This mixture turns into a very viscous gel. Flavour oil is added while the gel is being mixed. Mixing is continued until the core materials are thoroughly dispersed uniformly in the gel matrix. In some situations, the colloid gel may need two or more gelling polymers to obtain the desired properties of the gel matrix. The flavour oil stays in the gel matrix with reasonable stability due to the character of the gel matrix with the hydrophobic and hydrophilic nature of gel polymers. This colloidal gel matrix can be used in the gel form. Flavour oil is encapsulated in the gel matrix, which can be ground and mixed into the tabletting formulation.

A base formulation was developed to see if it was even possible to make tablet that was swallowable and would disintegrate rapidly in a glass of hot or warm water, to provide a drink of volume in the range 50-150 ml; preferably 80-120 ml. This was attempted using a directly-compressible grade of paracetamol which is coated with pre-gelatinised starch; together with phenylephrine (hydrochloride), magnesium stearate, microcrystalline cellulose and crospovidone; and producing a caplet-shaped tablet by a standard tabletting method.

| | |
|---|---|
| Paracetamol PGS | 500 mg |
| Phenylephrine HCl | 6.1 mg (URT aid) |
| Microcrystalline cellulose | 80 mg (binder) |
| Crospovidone | 80 mg (disintegration aid) |
| Magnesium stearate | 6 mg (pressing aid) |
| Total: | 672.1 mg |

A large number of spray-dried lemon flavours were obtained from suppliers and a satisfactory lemon flavour was obtained when these were added to the tablet mixes along with aspartame (38 mg) and citric acid (50 mg). However in every case the tablet mixes failed to tablet satisfactorily. The cause is believed to be a flavour oil released from the flavour under compressive loading, preventing the powder from binding satisfactorily.

It was apparent that an alternate flavouring technology would be required, one in which the oil would not be released under compression. 122 mg of a proprietary encapsulated lemon flavourant per tablet was used and it was found that this material did not affect the ability to tablet the mixed powders. A proprietary encapsulated blackcurrant flavourant also tabletted satisfactorily.

The use of an encapsulated flavourant permits the tabletting of flavourant oils at relatively high loading which was not possible before in a tablet weighing approximately 1 g.

EXAMPLES

Formulated examples are now given, by way of illustration.

| | mg/tab |
|---|---|
| Lemon Tablet Example 1 | |
| Paracetamol DC PGS | 529 |
| Guafenesin | 100 |
| Phenylephrine hydrochloride 450 | 6 |
| Encapsulated flavourant | 122 |
| Avicel PH101 | 100 |
| Crospovidone | 100 |
| Citric acid anhyd. | 50 |
| Aspartame | 38 |
| Magnesium Stearate | 12 |
| Yellow coloring agent | 5 |
| Total: | 1062 mg |
| Lemon tablet Example 2 | |
| Paracetamol DC PGS | 529 |
| Phenylephrine hydrochloride 450 | 6 |
| Encapsulated flavourant | 122 |
| Avicel PH101 | 80 |
| Crospovidone | 80 |
| Citric acid anhyd. | 50 |
| Aspartame | 38 |
| Magnesium Stearate | 6 |
| Yellow coloring agent | 5 |
| Total: | 916 mg |

It was found that both examples were excellent in terms of tabletting; in mechanical properties (including hardness and friability); in mouthfeel and taste when taken in the mouth as a tablet; in dissolution speed into warm or hot water to make a drink; in taste when thus dissolved, and drunk; and in cosmetic properties (including appearance and surface finish).

Lemon tablet Example 2 (three batches, 2A, 2B and 2C) was subjected to friability testing using the standard method of Ph Eur monograph, method 2.9.7. (10 tablets, 100 drops over 4 minutes, loss of tablet weight to abrasion determined. Percentage loss calculated giving friability value). It was further subjected to hardness testing using the standard method of Ph Eur monograph, method 2.9.8. (10 tablets, assessing resistance to crushing under diametrical loading). The results are shown on the following table, as Samples 2A, 2B and 2C.

In the table the time—0 mins, 15 mins, 30 mins . . . 150 mins—denotes when in a production run tablets were removed for testing. Samples 2A, 20 tablets in number, were taken out for a first production run at the stated times and were weighed, and the average weights calculated. These values are given in the first column headed 2A. 10 tablets were then subjected to the friability testing and the weight loss values are shown. The remaining 10 tablets were subjected to hardness testing and the mean compressive force at which failure takes place are shown.

The regime of testing was repeated with Sample 2B and Sample 3C and the results are again shown in the table.

In general it may be stated that tabletting gave a good consistency of tablet weight; that the friability of the tablets was low; and that the tablets were moderately hard. This is good in terms of robustness in manufacture and handling but also good in terms of speed dissolution. It is believed that a hard tablet promotes fast dissolution. On our dissolution tests it was observed that dissolution of the tablets in hot water was extremely fast: typically 70% of the paracetamol is released into hot water in the first 40 seconds of dissolution; and substantially all of it in the first minute.

| | Sample | | | | | | | | |
|---|---|---|---|---|---|---|---|---|---|
| | Mean tablet weight/mg | | | Friability/% | | | Hardness/kp | | |
| Mins | 2A | 2B | 2C | 2A | 2B | 2C | 2A | 2B | 2C |
| 0 | 0.9086 | 0.9233 | 0.9170 | 0.27 | 0.27 | 0.22 | 15.26 | 16.41 | 18.98 |
| 15 | 0.9148 | 0.9117 | 0.9224 | 0.22 | 0.26 | 0.24 | 15.66 | 16.19 | 15.64 |
| 30 | 0.9176 | 0.9171 | 0.9222 | 0.21 | 0.27 | 0.23 | 15.97 | 16.36 | 15.26 |
| 45 | 0.9132 | 0.9187 | 0.9194 | 0.26 | 0.27 | 0.23 | 15.97 | 17.23 | 16.42 |
| 60 | 0.9234 | 0.9188 | 0.9224 | 0.24 | 0.27 | 0.26 | 16.42 | 17.14 | 15.95 |
| 75 | 0.9107 | 0.9260 | 0.9244 | 0.24 | 0.26 | 0.25 | 16.30 | 17.18 | 15.96 |
| 90 | 0.9230 | 0.9275 | 0.9214 | 0.23 | 0.24 | 0.26 | 15.89 | 17.10 | 16.42 |
| 105 | 0.9227 | 0.9100 | 0.9195 | 0.25 | 0.24 | 0.23 | 16.84 | 16.15 | 15.99 |
| 120 | 0.9230 | 0.9130 | 0.9182 | 0.25 | 0.26 | 0.23 | 15.97 | 14.92 | 16.57 |
| 135 | 0.9158 | 0.9081 | 0.9136 | 0.26 | 0.28 | 0.26 | 16.42 | 14.81 | 16.27 |
| 150 | 0.9085 | 0.9165 | 0.9076 | 0.25 | 0.25 | 0.24 | 16.50 | 15.82 | 16.01 |

The invention claimed is:

1. A tablet comprising:
   granulated paracetamol (acetaminophen) coated with pre-gelatinized starch;
   60-200 mg of crospovidone;
   at least 40 mg of an organic acid selected from the group consisting of citric acid or salt thereof, tartaric acid or salt thereof, malic acid or salt thereof, maleic acid or salt thereof, fumaric acid or salt thereof, ascorbic acid or salt thereof, and any combination thereof;
   at least 60 mg of microcrystalline cellulose;
   at least 80 mg of an encapsulated flavorant;
   at least 20 mg of a sweetening agent; and
   wherein the granulated paracetamol coated with pre-gelatinized starch comprises at least 300 mg of the active agent paracetamol; and
   wherein the weight of the tablet is less than or equal to 1,200 mg.

2. The tablet of claim 1, wherein the organic acid is citric acid anhydrous.

3. The tablet of claim 1, wherein the sweetening agent is aspartame.

4. The tablet of claim 3, wherein the organic acid is citric acid anhydrous.

5. The tablet of claim 1, wherein the granulated paracetamol coated with pre-gelatinized starch comprises 500-550 mg of the active agent paracetamol.

6. The tablet of claim 1 further comprising an upper respiratory tract (URT) aid selected from the group consisting of dextromethorphan, noscapine, ethyl morphine, theobromine, pholcodine, codeine, phenylephrine, pseudoephedrine, diphenhydramine, guaifenesin, ambroxol, and any combination thereof.

7. The tablet of claim 1, wherein the weight of the tablet is less than or equal to 1,100 mg.

8. The tablet of claim 2, wherein the weight of the tablet is less than or equal to 1,100 mg.

* * * * *

UNITED STATES PATENT AND TRADEMARK OFFICE
CERTIFICATE OF CORRECTION

| | | |
|---|---|---|
| PATENT NO. | : 8,568,775 B2 | Page 1 of 1 |
| APPLICATION NO. | : 12/295771 | |
| DATED | : October 29, 2013 | |
| INVENTOR(S) | : Field | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 937 days.

Signed and Sealed this
Second Day of June, 2015

Michelle K. Lee
*Director of the United States Patent and Trademark Office*